United States Patent
Harding et al.

(10) Patent No.: US 10,730,178 B2
(45) Date of Patent: Aug. 4, 2020

(54) ENSURING OPERATOR ENGAGEMENT IN AN EXOSKELETON BIONIC DEVICE

(71) Applicant: Ekso Bionics, Inc., Richmond, CA (US)

(72) Inventors: Nathan Harding, Oakland, CA (US); Niel McCaffrey, Mill Valley, CA (US); Kurt Amundson, Berkeley, CA (US); Reuben Sandler, Berkeley, CA (US); Adam Zoss, Berkeley, CA (US); Katherine Strausser, Berkeley, CA (US)

(73) Assignee: Ekso Bionics, Inc., Richmond, CA (US)

( * ) Notice: Subject to any disclaimer, the term of this patent is extended or adjusted under 35 U.S.C. 154(b) by 296 days.

(21) Appl. No.: 15/571,201

(22) PCT Filed: May 4, 2016

(86) PCT No.: PCT/US2016/030771
§ 371 (c)(1),
(2) Date: Nov. 1, 2017

(87) PCT Pub. No.: WO2016/179275
PCT Pub. Date: Nov. 10, 2016

(65) Prior Publication Data
US 2018/0264642 A1 Sep. 20, 2018

Related U.S. Application Data

(60) Provisional application No. 62/157,241, filed on May 5, 2015.

(51) Int. Cl.
*A61H 3/00* (2006.01)
*B25J 9/00* (2006.01)
(Continued)

(52) U.S. Cl.
CPC .......... *B25J 9/0006* (2013.01); *A61H 1/0255* (2013.01); *A61H 3/00* (2013.01);
(Continued)

(58) Field of Classification Search
CPC combination set(s) only.
See application file for complete search history.

(56) References Cited

U.S. PATENT DOCUMENTS

| 4,697,808 A | 10/1987 | Larson et al. |
| 5,020,790 A | 6/1991 | Beard et al. |

(Continued)

FOREIGN PATENT DOCUMENTS

| CN | 1956692 | 5/2007 |
| CN | 102906623 | 1/2013 |

(Continued)

*Primary Examiner* — Masud Ahmed
(74) *Attorney, Agent, or Firm* — Diederiks & Whiteclaw, PLC

(57) ABSTRACT

An operator supervising a wearer of an exoskeleton is verified by performing a verification routine on the operator using the exoskeleton. If the verification routine is unsuccessful, the exoskeleton is caused to follow a pre-established response routine. If the verification routine is successful, movement of the exoskeleton is allowed.

23 Claims, 2 Drawing Sheets

(51) Int. Cl.
  *A61H 1/02* (2006.01)
  *G16H 40/63* (2018.01)
  *A61H 3/02* (2006.01)
  *A61B 5/1172* (2016.01)

(52) U.S. Cl.
  CPC ............ *G16H 40/63* (2018.01); *A61B 5/1172* (2013.01); *A61H 3/02* (2013.01); *A61H 2201/0176* (2013.01); *A61H 2201/0184* (2013.01); *A61H 2201/0188* (2013.01); *A61H 2201/164* (2013.01); *A61H 2201/165* (2013.01); *A61H 2201/1676* (2013.01); *A61H 2201/5007* (2013.01); *A61H 2201/5012* (2013.01); *A61H 2201/5028* (2013.01); *A61H 2201/5041* (2013.01); *A61H 2201/5043* (2013.01); *A61H 2201/5048* (2013.01); *A61H 2201/5058* (2013.01); *A61H 2201/5064* (2013.01); *A61H 2201/5082* (2013.01); *A61H 2201/5084* (2013.01); *A61H 2201/5092* (2013.01); *A61H 2201/5097* (2013.01); *A61H 2205/088* (2013.01); *A61H 2205/102* (2013.01); *Y10S 901/01* (2013.01)

(56) References Cited

U.S. PATENT DOCUMENTS

| | | | |
|---|---|---|---|
| 7,591,078 B2 | 9/2009 | Crampton | |
| 7,901,368 B2 | 3/2011 | Flaherty et al. | |
| 8,012,107 B2 | 9/2011 | Einav et al. | |
| 8,096,965 B2 | 1/2012 | Goffer et al. | |
| 8,527,143 B2 | 9/2013 | Tan | |
| 2007/0282228 A1* | 12/2007 | Einav | A63B 21/4021 601/33 |
| 2009/0210093 A1* | 8/2009 | Jacobsen | A61H 3/008 700/260 |
| 2010/0113980 A1* | 5/2010 | Herr | A61F 2/60 600/587 |
| 2010/0114329 A1* | 5/2010 | Casler | B25J 19/0008 623/24 |
| 2011/0082566 A1* | 4/2011 | Herr | A61F 2/60 623/24 |
| 2012/0101415 A1 | 4/2012 | Coffer et al. | |
| 2012/0242698 A1* | 9/2012 | Haddick | G02B 27/0093 345/633 |
| 2012/0329611 A1 | 12/2012 | Bouchard et al. | |
| 2014/0012164 A1 | 1/2014 | Tanaka | |
| 2014/0100493 A1 | 4/2014 | Craig et al. | |
| 2014/0142475 A1 | 5/2014 | Goldfarb et al. | |
| 2014/0371871 A1* | 12/2014 | Farina | B25J 9/1612 623/24 |
| 2015/0012111 A1* | 1/2015 | Contreras-Vidal | A61B 5/4851 623/25 |
| 2015/0045703 A1* | 2/2015 | Strausser | A61H 3/00 601/35 |
| 2015/0051519 A1* | 2/2015 | Morbi | A61H 1/02 601/26 |
| 2015/0119998 A1* | 4/2015 | Garrec | B25J 9/0006 623/57 |
| 2016/0250093 A1* | 9/2016 | Koren | A61F 2/60 623/30 |
| 2017/0202724 A1* | 7/2017 | De Rossi | A61H 3/00 |

FOREIGN PATENT DOCUMENTS

| | | |
|---|---|---|
| CN | 103622792 | 3/2014 |
| WO | 2014/159577 | 10/2014 |

* cited by examiner

ENSURING OPERATOR ENGAGEMENT IN AN EXOSKELETON BIONIC DEVICE

CROSS REFERENCE TO RELATED APPLICATIONS

This application represents a National Stage application of PCT/US2016/030771, filed May 4, 2016 and titled "Ensuring Operator Engagement in an Exoskeleton Bionic Device", which claims the benefit of U.S. Provisional Patent Application Ser. No. 62/157,241, filed on May 5, 2015 and titled "Ensuring Operator Engagement in an Exoskeleton Bionic Device". The entire content of these applications is incorporated herein by reference.

BACKGROUND OF THE INVENTION

The present invention pertains to exoskeletons and, more particularly, to ensuring that an operator is present during operation of an exoskeleton.

When an exoskeleton is used by a disabled patient, the patient's use of the exoskeleton is sometimes overseen by a physical therapist or other trained operator. In such cases, it is important that the operator be in close proximity to the patient and exoskeleton. It is also important that the operator pay close attention to the patient and exoskeleton. As a result, there is a need in the art for systems and methods that help ensure that an operator is in proximity to and is paying attention to an exoskeleton and wearer during use of the exoskeleton by the wearer.

SUMMARY OF THE INVENTION

The present invention is directed to systems and methods for ensuring operator engagement during use of an exoskeleton. An operator supervising a wearer of the exoskeleton is verified by performing a verification routine on the operator using the exoskeleton. If the verification routine is unsuccessful, the exoskeleton is caused to follow a pre-established response routine. If the verification routine is successful, movement of the exoskeleton is allowed.

In one embodiment, the verification routine is performed after the exoskeleton is turned on and before any movement of the exoskeleton takes place. In another embodiment, the exoskeleton is commanded to perform a movement, and the verification routine is performed after the command. If the verification routine is successful, the exoskeleton performs the commanded movement. In still another embodiment, the exoskeleton is commanded to perform a series of movements, and the verification routine is performed after a first movement of the series of movements. If the verification routine is successful, a second movement of the series of movements is performed. In another embodiment, the exoskeleton is commanded to perform a series of movements, and the verification routine is performed periodically during the series of movements. If one of the verification routines is unsuccessful, the series of movements is ceased.

In a further embodiment, the exoskeleton includes a user interface that is not reachable by a hand of the wearer. The verification routine is performed by presenting a notification to the operator on the user interface, and dismissal of the notification constitutes a successful verification routine. In a still further embodiment, the verification routine is performed by determining whether a key is coupled to the exoskeleton. The key being coupled to the exoskeleton constitutes a successful verification routine.

In one embodiment, the exoskeleton includes a button that is not reachable by a hand of the wearer. The verification routine is performed by prompting the operator to press the button, and pressing of the button constitutes a successful verification routine. In some embodiments, the button is one of a plurality of buttons, and the verification routine is performed by prompting the operator to press the plurality of buttons in a defined order. Pressing of the plurality of buttons in the defined order constitutes a successful verification routine. In other embodiments, the operator is prompted to press the button a specified number of times, and pressing of the button the specified number of times constitutes a successful verification routine.

In another embodiment, the exoskeleton includes a sensor, and the verification routine is performed by sensing whether the operator is proximate to the exoskeleton using the sensor. A determination that the operator is proximate to the exoskeleton constitutes a successful verification routine. The sensor can be a contact or non-contact sensor. In one embodiment, the exoskeleton includes a handle, and the sensor is a contact sensor that is coupled to or integrated with the handle. In such an arrangement, the sensor senses whether a hand of the operator is in contact with the handle.

In a further embodiment, data is transmitted between the exoskeleton and a remote signaling device. The verification routine is performed by determining whether the remote signaling device is proximate to the exoskeleton, and a determination that the remote signaling device is proximate to the exoskeleton constitutes a successful verification routine. In some embodiments, the remote signaling device includes a contact sensor that senses whether a hand of the operator is in contact with the remote signaling device. A determination that the remote signaling device is proximate to the exoskeleton and that the hand of the operator is in contact with the remote signaling device constitutes a successful verification routine.

In one embodiment, the verification routine is performed by prompting the operator to look at a particular location and measuring a response time of the operator using an eye-tracking sensor. The response time determines whether the verification routine is successful. In another embodiment, the verification routine involves performing a fingerprint, iris or voice scan on the operator to generate first biometric data and comparing the first biometric data to second biometric data corresponding to an authorized operator. A determination that the first biometric data matches the second biometric data constitutes a successful verification routine.

In some embodiments, the response routine includes ceasing movement of the exoskeleton. The response routine can further include causing the exoskeleton to sit or crouch if a predetermined time passes after movement of the exoskeleton ceases without a successful verification routine. In other embodiments, the response routine includes sounding an alarm, notifying emergency services or disabling use of the exoskeleton.

Additional objects, features and advantages of the invention will become more readily apparent from the following detailed description of preferred embodiments thereof when taken in conjunction with the drawings wherein like reference numerals refer to common parts in the several views.

DETAILED DESCRIPTION OF THE PREFERRED EMBODIMENTS

Detailed embodiments of the present invention are disclosed herein. However, it is to be understood that the disclosed embodiments are merely exemplary of the invention that may be embodied in various and alternative forms. The figures are not necessarily to scale, and some features may be exaggerated or minimized to show details of particular components. Therefore, specific structural and functional details disclosed herein are not to be interpreted as limiting, but merely as a representative basis for teaching one skilled in the art to employ the present invention.

Figure 1:
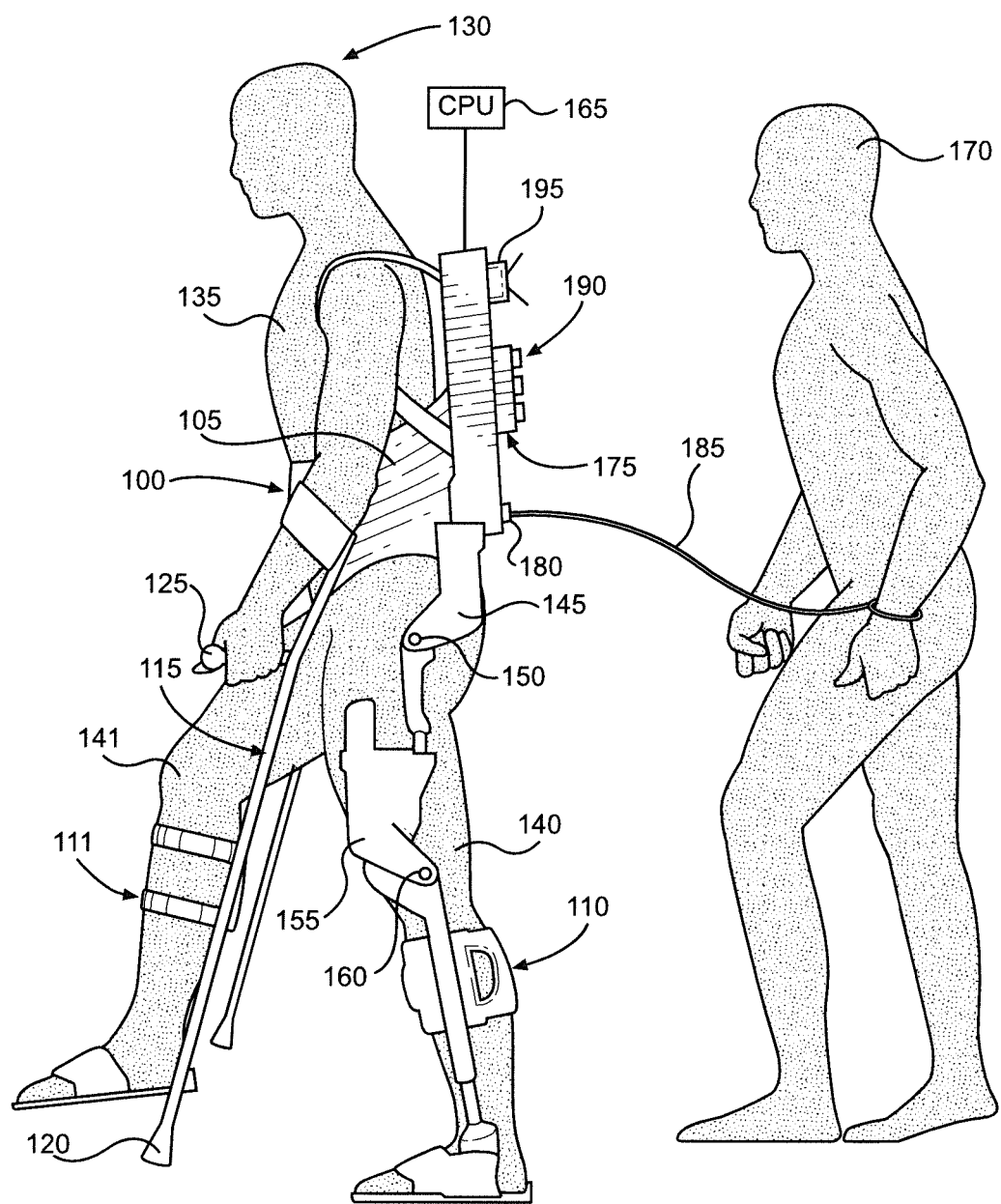
FIG. 1 is a side view of an exoskeleton, an exoskeleton wearer and an exoskeleton operator in accordance with a first embodiment of the present invention.

With initial reference to FIG. 1, there is shown an exoskeleton 100 having a torso support 105 and lower leg supports 110 and 111. Exoskeleton 100 is used in combination with a pair of crutches, a left crutch 115 of which includes a lower, ground-engaging tip 120 and a handle 125. In connection with this embodiment, through the use of exoskeleton 100, a patient (or, more generally, a user or wearer) 130 is able to walk. In a manner known in the art, torso support 105 is configured to be coupled to a torso 135 of patient 130, while leg supports 110 and 111 are configured to be coupled to lower limbs 140 and 141 of patient 130. Additionally, actuators are interposed between portions of leg supports 110 and 111 as well as between leg supports 110 and 111 and torso support 105, with these actuators being configured to shift leg supports 110 and 111 relative to torso support 105 to enable movement of lower limbs 140 and 141 of patient 130. In some embodiments, torso support 105 can be quite small and comprise a pelvic link (not shown), which wraps around the pelvis of patient 130. In the example shown in FIG. 1, the actuators are specifically shown as a hip actuator 145, which is used to move a hip joint 150 in flexion and extension, and as a knee actuator 155, which is used to move a knee joint 160 in flexion and extension. Actuators 145 and 155 are controlled by a controller (or control system or CPU) 165 in a plurality of ways known to one skilled in the art of exoskeleton control. Although not shown in FIG. 1, various sensors are in communication with controller 165 so that controller 165 can monitor the orientation of exoskeleton 100. Such sensors can include, without restriction, encoders, potentiometers, accelerometer and gyroscopes, for example. In some embodiments, controller 165 is in either continuous or intermittent communication with, and transfers selected exoskeleton state data to, a data link (not shown). As certain additional structural particulars of exoskeletons can take various forms, are known in the art and are not part of the present invention, they will not be detailed further herein.

An operator 170 supervises and assists patient 130 while patient 130 is using exoskeleton 100, i.e., operator 170 spots patient 130. As discussed above, it is important that operator 170 remain in close proximity to and pay close attention to patient 130 and exoskeleton 100. This helps ensure that the use of exoskeleton 100 by patient 130 is appropriate and effective. The engagement of operator 170 with patient 130 and exoskeleton 100 can be disrupted both voluntarily and involuntarily. In either case, it is an object of the present invention to provide a way by which engagement of operator 170 is verified, with exoskeleton 100 responding as appropriate. For purposes of the present invention, verification is divided into three categories.

The first verification category is verification of responsibility, which occurs at startup of exoskeleton 100. In one embodiment, a notification is provided to operator 170 on a screen (not visible) of a user interface 175 when exoskeleton 100 is first turned on and booted up. The notification must be dismissed or otherwise addressed by operator 170 prior to use of exoskeleton 100 by patient 130. In order to prevent patient 130 from dismissing the notification, user interface 175 is located on the rear of exoskeleton 100. This also facilitates use of user interface 175 by operator 170 while operator 170 is spotting patient 130. The notification can take various forms. For instance, the notification can be a message requesting that operator 170 acknowledge that operator 170 should be present and attentive at all times. The notification can include other or additional terms if desired. In another embodiment, operator 170 is provided with a physical key 180, which operator 170 keeps under his or her control. Key 180 can take the form of a portion of exoskeleton 100 that exoskeleton 100 needs in order to operate, such as a fuse or user interface 175. Of course, key 180 can also take the form of a more traditional key. Key 180 can optionally be coupled to operator 170 through a cord or lanyard 185, for example, to ensure that operator 170 remains in proximity to exoskeleton 100. If operator 170 moves too far from exoskeleton 100 or vice versa, cord 185 will become taut, with additional movement exerting a pulling force on operator 170, thereby alerting operator 170 and optionally causing key 180 to become dislodged. If key 180 is dislodged, exoskeleton 100 can respond in a number of different ways, such as ceasing movement and shutting down, as will be discussed more fully below.

The second verification category is verification of presence and attentiveness. This verification can take place once each time a movement or series of movements is initiated or in an ongoing fashion. In one embodiment, user interface 175 includes a plurality of buttons (collectively labeled 190), at least one of which must be pressed in order for exoskeleton 100 to perform a desired movement, such as walking. Buttons 190 can be physical or digital. Accordingly, for purposes of the present invention, the term "pressed" includes both depressing a physical button as well as touching or tapping a button on a touchscreen. If ongoing verification is desired, at least one of buttons 190 must be periodically re-pressed during the movement of exoskeleton 100 to verify continued presence of operator 170. The period between presses can be fixed or random. So long as buttons 190 are not reachable by patient 130, operator 170 will need to be present during use of exoskeleton 100. Although user interface 180 is shown and described as having a plurality of buttons 190, the above verification can be accomplished using a single button. Alternatively, to make use of the plurality of buttons 190, exoskeleton 100 can require that a specific one of buttons 190 is pressed, with this button being randomly chosen each time. To indicate which of buttons 190 should be pressed by operator 170, the chosen button can be lit by a light emitting diode (LED), for example. Of course, exoskeleton 100 can instead require that two or more of buttons 190 be pressed in a fixed order. In another variation, a certain number of button presses of one or more of buttons 190 is required, with the number indicated by illuminating a corresponding number of LEDs, for example. This variation can also be used when a single button is provided.

In another embodiment, presence verification is accomplished through the use of sensors. Again, such verification can take place once each time a movement or series of movements is initiated or in an ongoing fashion. There are a variety of methods known in the art for determining physical proximity including, for instance, radar, infrared imaging, acoustics, contact or proximity capacitance, force sensitive resistors, piezoresistive touch sensitive materials, light time of flight measurements and temperature sensing. In connection with the present invention, exoskeleton 100 can make use of one or more of these proximity detection methods to check whether operator 170 is located behind exoskeleton 100 and respond as appropriate. With reference again to FIG. 1, exoskeleton 100 includes a sensor 195, or more specifically a non-contact sensor, which, by way of example, variously represents one or more of the following types of non-contact sensors: radar; infrared; acoustics; and light time of flight.

Figure 2:
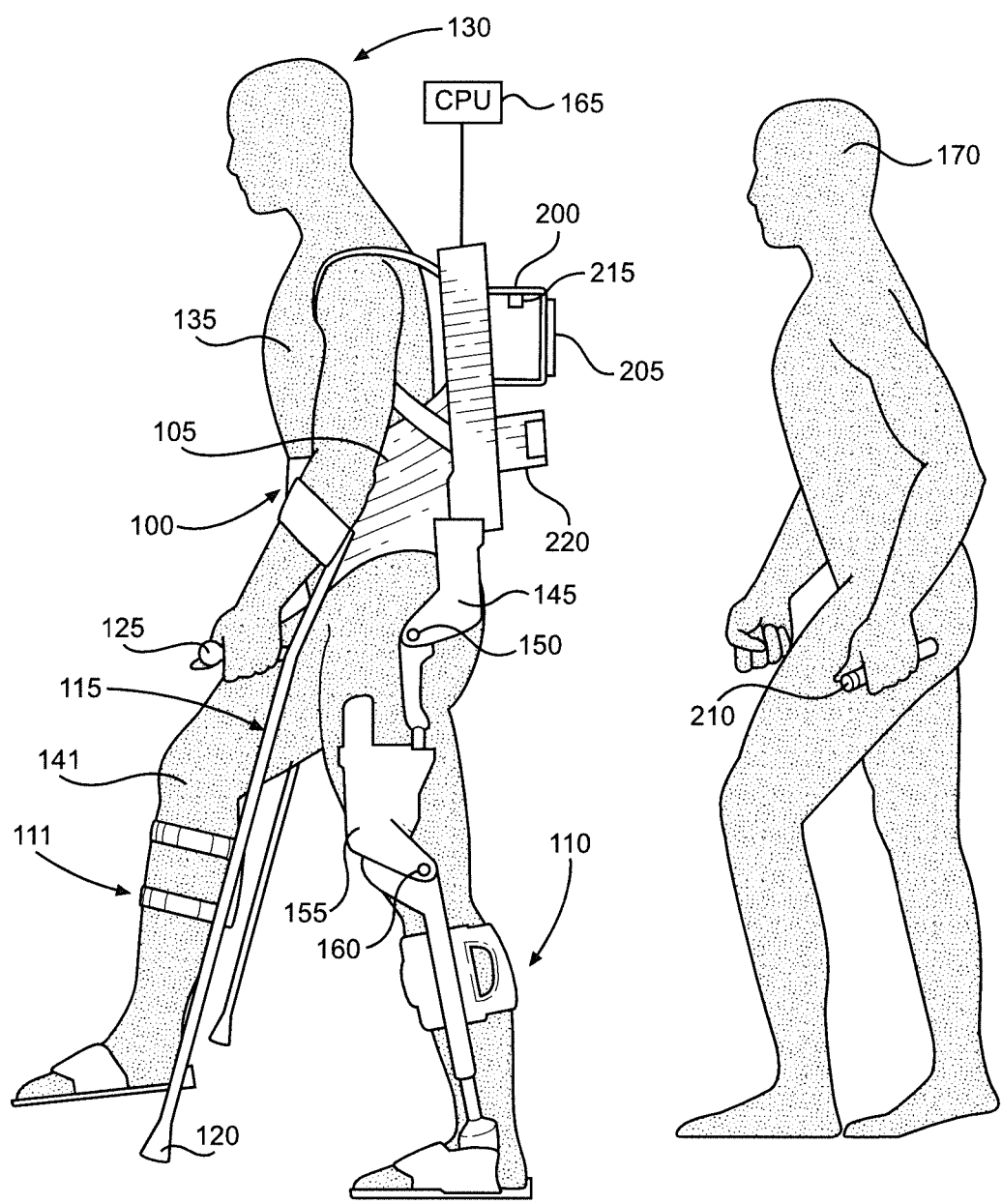
FIG. 2 is a side view of an exoskeleton, an exoskeleton wearer and an exoskeleton operator in accordance with a second embodiment of the present invention.

In FIG. 2, an exoskeleton 100' includes handles (one of which is labeled 200) and a sensor 205. Sensor 205 is a contact sensor and, by way of example, represents one or more of the following types of contact sensors: capacitance; force sensitive resistors; piezoresistive touch sensitive materials; and temperature sensing. Sensor 205 is coupled to or integrated with handle 200 in order to sense a grip of operator 170 on handle 200. As a result, sensor 205 and handle 200 can function as a dead man's switch, i.e., if operator 170 lets go of handle 200, sensor 205 sends a signal to a controller 165' of exoskeleton 100' so that exoskeleton 100' can respond in an appropriate manner. If desired, an additional contact sensor can be used in connection with the other handle. However, it should be recognized that sensor 205 need not be coupled to or integrated with handle 205. For example, sensor 205 can be located on some other portion of the rear of exoskeleton 100'. Alternatively, sensor 205 can be integrated as part of a remote signaling device 210 held by operator 170 but otherwise functions in the same manner described above. In such an arrangement, exoskeleton 100' and remote signaling device 210 are preferably provided with a way to communicate wirelessly, e.g., by including corresponding data links. As a result, exoskeleton 100' can determine whether remote signaling device 210 is located nearby, with remote signaling device 210 indicating whether or not a hand of operator 170 is in contact with sensor 205. Remote signaling device 210 can also be used without sensor 205 such that communication between exoskeleton 100 and remote signaling device 210 simply indicates whether remote signaling device 210 is nearby. Regardless of whether contact or non-contact sensors are used, exoskeletons 100 and 100' are configured to determine whether an operator 170 is present and respond as appropriate. Accordingly, exoskeletons 100 and 100' are preferably configured not just to determine whether an object is located nearby or in contact with a sensor but also to determine whether this object is a person or a portion thereof. As such features are known in the art of proximity detection, they will not be detailed herein.

In a further embodiment, presence and attentiveness verification is accomplished by drawing the gaze of operator 170 to user interface 175 (or some other portion of exoskeleton 100) via an audio or visual cue and then measuring the response time of operator 170. This can be implemented using an eye-tracking sensor and appropriate software, for example, with this sensor being included as part of sensor 195. In another embodiment, a tactile, audio or visual cue is delivered, and operator 170 is required to respond using the handles of exoskeleton 100', which operator 170 is typically already holding. Preferably, the cue indicates which of the handles operator 170 must use to respond. In one example, when handle 200 is vibrated, operator 170 is required to respond by pressing a button 215 located on handle 200. As with the button-based verification described above, multiple inputs, either random or fixed, can be required of operator 170. For example, exoskeleton 100' can prompt operator to press button 215 twice and then press a button on the other handle once. Similarly, exoskeleton 100 can prompt operator 170 to look at multiple locations in a specific order while tracking the gaze of operator 170 using an eye-tracking sensor included in sensor 195.

One issue to consider in connection with the verification routines of the second category is that the routines should preferably not unduly distract operator 170 from engaging with patient 130 and exoskeleton 100. In other words, the verification routines of the present invention that are used when patient 130 and exoskeleton 100 are active should preferably not be too intrusive. To accomplish the goal of verifying presence and attention without unduly distracting operator 170, the verification routines that require a response from operator 170 (as opposed to simply sensing the presence of operator 170) are preferably relatively brief and not overly complex. To further minimize any potential distraction or allow for more complex verification routines, additional steps can be taken. For example, movement of exoskeleton 100 can be temporarily paused during verification. Similarly, if a periodic verification ends up being scheduled during a movement, the verification can be delayed until after the movement is complete. For instance, verification can be delayed until after a step is completed such that patient 130 and exoskeleton 100 are halted in a normal standing position. In addition, an indication that verification is taking place can be presented to patient 130 so that patient 130 is aware of what operator 170 is doing or why movement of exoskeleton 100 has stopped.

The third verification category is verification of a specific operator. This verification can take place once when exoskeleton 100 is first turned on and booted up, once each time a movement or series of movements is initiated or in an ongoing fashion. In one embodiment, as shown in FIG. 2, exoskeleton 100' includes a biometric sensor 220 configured to verify the identity of operator 170 through the use of fingerprint, iris or voice scanning, for example. In such an arrangement, the biometric data of operator 170 is compared to the biometric data of one or more authorized operators, with a match indicating that operator 170 is authorized. In general, such a system provides additional security.

If one of the verification routines described above is unsuccessful, exoskeleton 100 can perform any of a variety of different response routines. By unsuccessful, it is meant, for example, that key 180 has become dislodged or that operator 170 did not press the correct one of buttons 190. In one embodiment, exoskeleton 100 responds by ceasing movement. Exoskeleton 100 can also sound an alarm or adopt a more stable position, such as sitting or crouching if exoskeleton 100 is standing. These actions can occur in sequence, with the response escalating over time if operator 170 does not remedy the situation.

If the situation appears sufficiently serious, exoskeleton 100 can notify emergency services. This notification can occur automatically. Alternatively, exoskeleton 100 can prompt patient 130 to confirm or cancel the notification, with the notification being sent if no response is selected. In some embodiments, exoskeleton 100 provides a voice link between patient 130 and emergency services so that emergency services can talk to patient 130 and assess the severity of the situation. Also, in some embodiments, exoskeleton 100 can make use of its sensors to assess the severity of the situation and respond accordingly. For example, if exoskeleton 100 senses a rapid deceleration consistent with an impact, exoskeleton 100 can notify emergency services. If a sufficiently serious failure is detected, exoskeleton 100 can disable itself, thereby preventing further use. For example, if operator 170 is absent for a long duration, exoskeleton 100 can disable itself until re-enabled by a physical therapist or the exoskeleton manufacturer. Exoskeleton 100 can also disable itself if exoskeleton 100 is damaged in a fall, for example, with damage being assessed using contemporaneous sensor data or based on a self-check performed at a later time.

Preferably, the response to an unsuccessful verification routine depends on the particular routine. For example, if operator 170 fails to dismiss the notification described in connection with the first verification category, exoskeleton 100 can simply shut down after a predetermined time passes since no movement of exoskeleton 100 should have occurred. This same response is also applicable if the identity of operator 170 were never verified using biometric sensor 220, as described in connection with the third verification category. Of course, a different response can be used if the identity of operator 170 is verified one or more times but a subsequent verification is unsuccessful. This logic also applies to the second verification category. That is, if an initial verification routine fails, exoskeleton 100 can simply shut down but, if a subsequent verification routine fails, additional steps should be taken. Of course, if during use of exoskeleton 100 no unsuccessful verification routines occur, exoskeleton 100 can simply operate normally for the entire duration of its use. If an unsuccessful verification routine occurs but is quickly remedied, exoskeleton 100 can resume operating normally, although it may be desirable to require that operator 170 reinitiate whatever movement or series of movements was interrupted.

In general then, the present invention involves performing a verification routine on an exoskeleton operator with an exoskeleton. If the verification is successful, the exoskeleton continues operating as normal. If the verification routine is unsuccessful, the exoskeleton performs a response routine. In connection with the present invention, the exoskeleton operator is distinct from an exoskeleton user or wearer, i.e., a person cannot simultaneously be considered both an exoskeleton operator and an exoskeleton wearer. As discussed above, the verification routine can take place after the exoskeleton is turned on and before any movement takes place, after the exoskeleton is commanded to perform a movement or during a series of movements performed by the exoskeleton. Also, the verification routine can take place once or periodically. A variety of verification and response routines are described above along with the conditions that constitute success or failure of the verification routines.

Although certain of the above verification routines could potentially be circumvented by a determined patient or operator, these routines at least ensure that any such circumvention is done intentionally and with knowledge that it should not be done. Also, it should be recognized that there is some overlap in the verification categories described above. For example, if key 180 is controlled exclusively by operator 170, key 180 can be considered to verify a specific operator, as in the third category. When used with cord 185, key 180 can verify the presence of operator 170, as in the second category. Regardless, the present invention is not limited to the categories described above, which are simply presented to facilitate the explanation of certain embodiments of the invention.

Based on the above, it should be readily apparent that the present invention provides systems and methods that help ensure that an operator is in proximity to and is paying attention to an exoskeleton and wearer during use of the exoskeleton by the wearer. Although described with reference to preferred embodiments, it should be readily understood that various changes or modifications could be made to the invention without departing from the spirit thereof. In general, the invention is only intended to be limited by the scope of the following claims.

The invention claimed is:

1. A method of verifying an operator supervising a wearer of an exoskeleton, the method comprising:
   the wearer commanding the exoskeleton to perform a movement;
   after commanding the exoskeleton to perform the movement, beginning to perform a verification routine on the operator using the exoskeleton by: prompting the operator to perform an action, sensing that the operator or a remote signaling device is proximate the exoskeleton, or performing a scan on the operator; and
   a) responsive to the verification routine being unsuccessful, causing the exoskeleton to follow a pre-established response routine instead of the movement; or
   b) responsive to the verification routine being successful, performing the movement.

2. The method of claim 1, further comprising:
performing the verification routine after the exoskeleton is turned on and before any movement of the exoskeleton takes place.

3. The method of claim 1, further comprising:
1)
   a) commanding the exoskeleton to perform a series of movements, the series of movements including a first movement and a second movement;
   b) performing the first movement, wherein performing the verification routine includes performing the verification routine after performing the first movement; and
   c) performing the second movement if the verification routine is successful; or
2)
   a) commanding the exoskeleton to perform a series of movements, wherein performing the verification routine includes periodically performing the verification routine during the series of movements; and
   b) ceasing the series of movements if one of the verification routines is unsuccessful.

4. The method of claim 1, wherein:
1) the exoskeleton includes a user interface, which is not reachable by a hand of the wearer, the method further comprising performing the verification routine by presenting a notification to the operator on the user interface, wherein dismissal of the notification constitutes a successful verification routine; or
2) the exoskeleton includes a button, which is not reachable by a hand of the wearer, the method further comprising performing the verification routine by prompting the operator to press the button, wherein pressing of the button constitutes a successful verification routine.

5. The method of claim 1, wherein:
performing the verification routine includes determining whether a key is coupled to the exoskeleton; and
the key being coupled to the exoskeleton constitutes a successful verification routine.

6. The method of claim 4, wherein:
1) the exoskeleton includes a plurality of buttons, and the button is one of the plurality of buttons, the method further comprising prompting the operator to press the button by prompting the operator to press the plurality of buttons in a defined order, wherein pressing of the plurality of buttons in the defined order constitutes a successful verification routine; or 2)
  a) prompting the operator to press the button includes prompting the operator to press the button a specified number of times; and
  b) pressing of the button the specified number of times constitutes a successful verification routine.

7. The method of claim 1, wherein the exoskeleton includes a sensor, the method further comprising:
  performing the verification routine by sensing whether the operator is proximate to the exoskeleton using the sensor, wherein a determination that the operator is proximate to the exoskeleton constitutes a successful verification routine.

8. The method of claim 7, wherein the sensor is a non-contact sensor, the method further comprising:
  sensing whether the operator is proximate to the exoskeleton by sensing whether the operator is proximate to the exoskeleton using the non-contact sensor.

9. The method of claim 7, wherein the sensor is a contact sensor, the method further comprising:
  sensing whether the operator is proximate to the exoskeleton by sensing whether the operator is proximate to the exoskeleton using the contact sensor, wherein the exoskeleton includes a handle, and the contact sensor is coupled to or integrated with the handle, the method further comprising:
    sensing whether the operator is proximate to the exoskeleton by sensing whether a hand of the operator is in contact with the handle.

10. The method of claim 1, further comprising:
  transmitting data between the exoskeleton and a remote signaling device; and
  performing the verification routine by determining whether the remote signaling device is proximate to the exoskeleton, wherein a determination that the remote signaling device is proximate to the exoskeleton constitutes a successful verification routine, and the remote signaling device includes a contact sensor, the method further comprising:
    sensing whether a hand of the operator is in contact with the remote signaling device using the contact sensor, wherein a determination that the remote signaling device is proximate to the exoskeleton and that the hand of the operator is in contact with the remote signaling device constitutes a successful verification routine.

11. The method of claim 1, wherein:
  performing the verification routine includes prompting the operator to look at a particular location and measuring a response time of the operator; and
  the response time determines whether the verification routine is successful.

12. The method of claim 1, wherein:
  performing the verification routine includes performing a fingerprint, iris or voice scan on the operator to generate first biometric data and comparing the first biometric data to second biometric data corresponding to an authorized operator; and
  a determination that the first biometric data matches the second biometric data constitutes a successful verification routine.

13. The method of claim 1, wherein performing the response routine includes:
  1) ceasing movement of the exoskeleton;
  2) sounding an alarm;
  3) notifying emergency services; or
  4) disabling use of the exoskeleton.

14. The method of claim 13, wherein performing the response routine includes ceasing movement of the exoskeleton and further includes causing the exoskeleton to sit or crouch if a predetermined time passes after movement of the exoskeleton ceases without a successful verification routine.

15. A system for verifying an exoskeleton operator supervising an exoskeleton wearer, the system comprising:
  an exoskeleton configured to:
    receive a command from the wearer to perform a movement;
    starting to perform a verification routine on the exoskeleton operator after receiving the command to perform the movement by: prompting the operator to perform an action, sensing that the operator or a remote signaling device is proximate the exoskeleton, or performing a scan on the operator; and
    a) follow a pre-established response routine instead of the movement if the verification routine is unsuccessful; or
    b) perform the movement if the verification routine is successful.

16. The system of claim 15, wherein:
1)
  a) the exoskeleton includes a user interface that is not reachable by a hand of the exoskeleton wearer;
  b) the exoskeleton is configured to perform the verification routine by presenting a notification to the exoskeleton operator on the user interface; and
  c) dismissal of the notification constitutes a successful verification routine; or
2)
  a) the exoskeleton includes a button that is not reachable by a hand of the exoskeleton wearer;
  b) the exoskeleton is configured to perform the verification routine by prompting the exoskeleton operator to press the button; and
  c) pressing of the button constitutes a successful verification routine.

17. The system of claim 15, further comprising a key, wherein:
  the exoskeleton is configured to perform the verification routine by determining whether the key is coupled to the exoskeleton; and
  the key being coupled to the exoskeleton constitutes a successful verification routine.

18. The system of claim 15, wherein:
  the exoskeleton includes a sensor;
  the exoskeleton is configured to perform the verification routine by sensing whether the exoskeleton operator is proximate to the exoskeleton using the sensor; and
  a determination that the exoskeleton operator is proximate to the exoskeleton constitutes a successful verification routine.

19. The system of claim 18, wherein the sensor is a non-contact sensor for sensing when the exoskeleton operator is proximate to the exoskeleton.

20. The system of claim 18, wherein the sensor is a contact sensor, the exoskeleton includes a handle, and the contact sensor is coupled to or integrated with the handle.

21. The system of claim 15, further comprising a remote signaling device, wherein:

the exoskeleton is configured to perform the verification routine by determining whether the remote signaling device is proximate to the exoskeleton;

a determination that the remote signaling device is proximate to the exoskeleton constitutes a successful verification routine;

the remote signaling device includes a contact sensor;

the remote signaling device is configured to sense whether a hand of the exoskeleton operator is in contact with the remote signaling device using the contact sensor; and a determination that the remote signaling device is proximate to the exoskeleton and that the hand of the exoskeleton operator is in contact with the remote signaling device constitutes a successful verification routine.

22. The system of claim 15, wherein:

the exoskeleton includes an eye-tracking sensor;

the exoskeleton is configured to perform the verification routine by prompting the exoskeleton operator to look at a particular location and measuring a response time of the exoskeleton operator using the eye-tracking sensor; and the response time determines whether the verification routine is successful.

23. The system of claim 15, wherein:

the exoskeleton includes a biometric sensor;

the exoskeleton is configured to perform the verification routine by performing a fingerprint, iris or voice scan on the exoskeleton operator using the biometric sensor to generate first biometric data and comparing the first biometric data to second biometric data corresponding to an authorized operator; and a determination that the first biometric data matches the second biometric data constitutes a successful verification routine.

* * * * *